US006172040B1

(12) United States Patent
Naidu

(10) Patent No.: US 6,172,040 B1
(45) Date of Patent: Jan. 9, 2001

(54) IMMOBILIZED LACTOFERRIN ANTIMICROBIAL AGENTS AND THE USE THEREOF

(75) Inventor: A. Satyanarayan Naidu, 9200 Monte Vista Ave., #3, Montclair, CA (US) 91763

(73) Assignee: A. Satyanarayan Naidu, Montclair, CA (US)

(*) Notice: Under 35 U.S.C. 154(b), the term of this patent shall be extended for 0 days.

(21) Appl. No.: 09/322,700

(22) Filed: May 28, 1999

(51) Int. Cl.$^7$ .......................... A23B 4/20; A23L 3/3499; A23L 3/3526; A61K 38/40; A61L 2/18

(52) U.S. Cl. ...................... 514/6; 422/28; 422/32; 426/310; 426/322; 426/326; 426/332; 426/335; 426/532; 514/8; 514/21

(58) Field of Search ........................ 424/439, 442; 426/302, 310, 321, 322, 326, 332, 335, 532, 574, 652; 422/28, 32; 514/6, 8, 21; 530/395, 400, 810, 811, 812, 813, 814, 815, 816, 817

(56) References Cited

U.S. PATENT DOCUMENTS

| | | | |
|---|---|---|---|
| 4,667,018 | 5/1987 | Prieels et al. | 530/417 |
| 4,791,193 | 12/1988 | Okonogi et al. | 530/416 |
| 4,946,944 | 8/1990 | Frankinet et al. | 530/400 |
| 5,015,487 | * 5/1991 | Collison et al. | 426/332 |
| 5,147,853 | 9/1992 | Dosako et al. | 514/7 |
| 5,156,875 | 10/1992 | Monte | 426/532 |
| 5,179,197 | 1/1993 | Uchida et al. | 530/366 |
| 5,214,028 | 5/1993 | Tomita et al. | 514/6 |
| 5,296,464 | 3/1994 | Tomita et al. | 514/6 |
| 5,389,611 | 2/1995 | Tomita et al. | 514/6 |
| 5,543,392 | * 8/1996 | Tomita et al. | 514/8 |
| 5,573,801 | * 11/1996 | Wilhoit | 426/326 |
| 5,606,086 | 2/1997 | Dosako et al. | 556/138 |
| 5,656,591 | 8/1997 | Tomita et al. | 514/6 |
| 5,834,424 | 11/1998 | Valenti et al. | 514/8 |

FOREIGN PATENT DOCUMENTS

| | | |
|---|---|---|
| 568200 | * 11/1993 | (EP) . |
| 2099065 | 12/1997 | (RU) . |

OTHER PUBLICATIONS

Harper et al., Dairy Technology and Engineering. Westpont: The Avi Publ. Co., Inc. pp. 20–23, 28–37 1976.*

Naidu, A.S. et al. "Milk lactoferrin—natural microbial blocking agent (MBA) for food safety",*Environ, & Nutri. Interac.*, 2: 35–50, 1998.

Naidu, A.S. et al., "Influence of Lactoferrin on Host—Microbe Interactions", *Lactoferrin: Interactions and Biological Functions*, Chapter 17, edited by T.W. Hutchins and B. Lönnerdal, Humana Press Inc. Totowa, NJ, pp. 259–275, 1997.

Alugupalli, K.R. et al., "Lactoferrin interaction with Actinobacillus actinomycetemcomitans", *Oral Microbiol. Immunol.*, 10: 35–41, 1995.

Naidu, A.S. et al., "Lactoferrin Interaction with Salmonellae Potentiates Antibiotic Susceptibility in vitro",*Diagn. Microbiol. Infect. Dis.*, 20: 69–75, 1994.

Alugupalli, K.R. et al., "Effect of lactoferrin on interaction of Prevotella intermedia with plasma and subepithelial matrix proteins", *Oral Microbiol. Immunol.*, 9: 174–179, 1994.

Gerlach, D. et al., "Identification of a Novel Lectin in Streptococcus pyrogenes and Its Possible Role in Baterial Adherence to Pharyngea Cells", *Current Microbiology*, 28: 331–338, 1994.

Erdei, J. et al., "Lactoferrin Binds to Porins OmpF and OmpC in Escherichia coli", *Infection and Immunity*, p. 1236–1240, Apr. 1994.

Paulsson, M.A. et al. "Thermal Behavior of Bovine Lactoferrin in Water and Its Relation to Bacterial Interaction and Antibacterial Activity", *J. Dairy Sci.*, 76:3711–3720, 1993.

Naidu, S.S. et al., "Relationship between Antibacterial Activity and Porin Binding of Lactoferrin in Eschericha coli and Salmonella typhimurium", *Antimicrobial Agents and Chemotherapy*, 37(2): 240–245, Feb. 1993.

Tigyi, Z. et al., "Lactoferrin–Binding Proteins in Shigella flexneri", *Infection and Immunity*, 60(7): 2619–2626, Jul. 1992.

Naidu, A.S. et al., "Indentification of a human lactoferrin–binding protein in Staphylococcus aureus", J. Med. Microbiol., 36: 177–183, 1992.

Kishore, A.R. et al., "Detection of bacterial interaction with lactoferrin by an enzyme–linked ligand binding assay (ELBA)", *J. Med. Microbiol.*, 37: 341–345, 1992.

Kalfas, S. et al., "Laminin binding to Prevotella intermedia", *Oral Microbiol. Immunol.*, 7: 235–239, 1992.

Gado, I. et al., "Correlation between Human Lactoferrin Binding and Colicin Susceptibility in Escherichia coli", *Antimicrobial Agents and Chemotherapy*, 35(12): 2538–2543, Dec. 1991.

Kishore, A.R. et al., "Specific binding of lactoferrin to Aeromonas hydrophila", *FEMS Microbiology Letters*, 83:115–120, 1991.

Kalfas, S. et al., "Human lactoferrin binding to Porphyromonas gingivalis, Prevotella intermedia and Prevotella melaninogenica", *Oral Microbiol. Immunol.*, 6: 350–355, 1991.

(List continued on next page.)

*Primary Examiner*—Jeffrey E. Russel
(74) *Attorney, Agent, or Firm*—Pretty & Schroeder, P.C.

(57) ABSTRACT

Disclosed is a method for treating products, such as meat products, with immobilized lactoferrin to reduce microbial contamination. The lactoferrin is immobilized on a naturally occurring substrate, preferably a galactose-rich polysaccharide. In some embodiments, the lactoferrin is applied as an aqueous solution containing a mixture of the immobilized lactoferrin and native lactoferrin, and a buffer system that includes a physiologically acceptable acid, such as citric acid, a physiologically acceptable base, such as sodium bicarbonate, and a physiologically acceptable salt, such as sodium chloride.

80 Claims, No Drawings

OTHER PUBLICATIONS

Naidu, A.S. et al., "Human lactoferrin binding in clinical isolates of *Staphylococcus aureus*", *J. Med. Microbiol.*, 34: 323–328, 1991.

Naidu, S.S. et al., "Specific binding of lactoferrin to *Escherichia coli* isolated from human intestinal infections", *APMIS*, 99: 1142–1150, 1991.

Naidu, A.S. et al., "Bovine Lactoferrin Binding to Six Species of Coagulase–Negative Staphylococci Isolated from Bovine Intramammary Infections", *J. Clinical Microbiol.*, 28(10): 2312–2319, 1990.

* cited by examiner

US 6,172,040 B1

IMMOBILIZED LACTOFERRIN ANTIMICROBIAL AGENTS AND THE USE THEREOF

BACKGROUND OF THE INVENTION

1. Field of the Invention

This invention relates to the chemical arts. In particular, it relates to antimicrobial agents and their use.

2. Discussion of the Related Art

Prior to slaughter, the edible tissues of a healthy meat animal are essentially sterile. Various innate host defense mechanisms at the external and internal organ surfaces create an effective barrier and prevent microorganisms from invading a live animal. As soon as the animal is slaughtered, however, the natural defenses against invading microbes virtually disappear, and the exposed tissues become highly susceptible to microbial colonization and proliferation. Meat of the freshly slaughtered animal is prone to contamination with a variety of bacterial species, influenced by the degree of sanitation practiced during the meat processing and packing operations.

The economic impact of food-borne pathogenic outbreaks and the shorter than desired shelf life of refrigerated products, even vacuum packaged refrigerated products, has necessitated the search for an effective antimicrobial system for the meat industry. The recent occurrence of verotoxic *Eschierichia coli* (*E. coli*) serotype O157:H7 in ground beef causing hemolytic uremic syndrome highlighted this long-standing problem, in foods and, especially, meats. It has prompted a major review of safety issues in the food industry and a call for improved methods for preventing microbial contamination. Various methods are currently in practice to control *Eschanchia coli* and other microbial contamination in foods, but, unfortunately, they suffer from a variety of drawbacks.

For example, in the meat industry, acid washing of beef carcasses is currently being employed as a microbial intervention. However, recent studies have shown that certain types of *E. coli*, such as the verotoxic strains of serotype O157:H7 and vancomycin-resistant strains of *Enterococcus faeciumi*, can survive acid conditions, while at the same time produce harmful toxins. The meat industry is also irradiating meat in an attempt to control pathogens and food spoilage organisms. However, studies have shown that although irradiation appears to be effective at killing some types of *E. coli*, there are still various other microorganisms, including strains of *Brochothrix thermospacta* and *Bacillis pumilus*, known to be radiation resistant and thus able to survive such processes. Irradiation also can produce undesirable changes in the texture and/or organoleptic quality of beef. Further, both of these methods are cidal processes that kill microorganisms leaving endotoxins, microbial debris and other proinflammatory substances which can cause undesirable immunological reactions in the host. Finally, neither of these methods excludes the possibility of post-processing contamination once the beef is treated for microbial contaminants.

Under certain conditions, it is possible to control microbes, including *E. coli*, using such well known antimicrobial agents as acids, salts, oxidative agents, antibiotics, bacteriocins, and the like. Typically, the mode of action of these agents is cidal—the direct killing of the microbes— or stasis—the inhibition of microbial growth-multiplication. Another mode of action for conventional antimicrobial agents is opsonization. The agents intervene by promoting microbial phagocytosis by macrophages.

Certain cellular research relating to the mechanisms of microbial biosurface interactions has led to the identification of another mode of action, microbial blocking, and a new class of antimicrobial agents, microbial blocking agents (MBAs). MBAs are naturally occurring biological substances that block microbial adhesion-colonization, retard growth-multiplication, and neutralize the adverse effects of proinflammatory cell debris.

It has not proved possible to apply such microbial blocking agents during meat packing or other food processing conditions, because of the difficulty of delivering a biofunctionally active and structurally stable MBA to the food product to be treated. The difficulty is compounded when the food product is a meat product, because a controlled milieu is required for a broad-spectrum activity of MBA to block various microorganisms on a chemically complex and heterogenous meat tissue.

Lactoferrin (LF) is an iron-bindinig glyco-protein present in milk and various mammalian secretions (e.g. saliva, tears, mucus, and seminal fluids). Crystallographic studies of LF indicate a bilobate structure (N-terminus and C-terminus lobes) with one iron-binding site in each lobe. LF has ability to reversibly bind two $Fe^{3+}$ ions per lobe in coordination with two $CO_3^{2-}$ ions. LF can release the bound iron in a fully reversible manner, either on exposure to lowered pH (below 4.0) or on receptor binding. This high affinity for iron is linked to many of its biological functions including antimicrobial effects. Various laboratory studies have reported that the structural integrity of LF is critical for its antimicrobial effects against bacteria, fungi, protozoa, and viruses.

However, the activity of LF, like the activity of most proteins, is highly dependent on the three-dimensional or tertiary structure of the protein. If the protein does not have the proper conformation its activity is diminished or lost. LF's instability limits it usefulness. Milieu conditions such as metals (iron in particular), carbonic ions, salts, pH and conductivity affect the antimicrobial properties of LF. In addition, protein isolation procedures, storage, freezing-thawing, can adversely affect the biofunctionality of LF. Consequently, before LF can be used for commercial application, it would be expected to become denatured or inactivated, and lose its antimicrobial properties.

In fact, under certain conditions, when the LF molecule is degraded or denatured, cationic peptide fragments are generated. These cationic peptides exhibit a non-specific antimicrobial activity, making them absolutely unsuitable as an ingredient in a food product. The consumer of a food product does not want to ingest a non-specific antimicrobial agent, because of the agent's adverse affect on the desirable microbes always present in a human body.

Thus, an antimicrobial agent is needed for blocking microbial contamination in foods, and meats in particular, that does not pose the undesired affects of cidal antimicrobial systems but that also exhibits carry through properties for the prevention of post-processing food contamination.

SUMMARY OF THE INVENTION

The present invention relates to a method for treating products with a sufficient amount of lactofeltin to reduce microbial contamination and the immobilized lactofenrin used in the process. More particularly, the present invention relates to immobilized lactofeltin and mixtures of immobilized lactofenrin and native lactoferrin having increased antimicrobial activity against a wide variety of bacteria and other food spoilage as well as increased stability for use in various stages of food processing, and a method for treating foods, and particularly meats, such as beef, pork and poultry products. The method is of use in preventing microbial contamination by a wide variety of microbes including enterotoxigenic *Escherichia coli*, enteropathogenic *Escherichia coli, Shigella dysenteriae, Shigella flexneri, Salmonella typhimurium, Salmonella abony, Salmonella dublin, Salmonella hartford, Salimonella kentucky, Salmonella panama, Salmonella pullorum, Salmonella restock, Salmonella thompson, Salmonella virschow, Campylobacter jejuni, Aeromonas hydrophila, Staphylococcus aureus, Staphylococcus hyicus, Staphylococcuis epidermidis, Staphylococcus hominis, Staphylococcus warneri, Staphylococcus xylosus, Staphylococcus chromogenes, Bacillus cereus, Bacillus subtilis, Candida albicans*, and such radiation-resistant bacteria as: *Brochothrix thermospacta, Bacillus pumilus, Enterococcus faecium, Deinococcus radiopugnans, Deinococcus radiodurans, Deinobacter grandis, Acinetobacter radioresistens, Methylobacterium radiotolerans*. It is of particular use in preventing microbial contamination by verotoxic *Escharichia coli*, including serotype O157:H7.

The lactoferrin is immobilized on a naturally occurring substrate via the N-terminus region of the lactoferrin. Suitable substrates include proteins, polysaccharides, cellulose, nucleic acids, nucleotides, and lipids. Preferred substrates include collagen, gelatin, fibronectin, casein, mucin, heparan-sulfate, carrageenan, deoxyribonucleic acid, adenosine triphosphate or a triglyceride, and galactose-rich polysaccharide being most preferred.

In some embodiments, the lactoferrin is applied as an aqueous solution containing a mixture of the immobilized lactoferrin and native lactoferrin, where the concentration of the mixture in the solution is from about 0.001 to about 2.5% wt/vol and the ratio of immobilized lactoferrin to native lactofenrin in the mixture is from about 1:1 to about 1:10, preferably about 1:1 to 1:5, and most preferably about 1:1. And in some embodiments, the mixture contains about 1% wt/vol immobilized lactoferrin and about 1% wt/vol native lactoferrin.

In some embodiments, the aqueous solution further includes a buffer system that contains a physiologically acceptable acid, such as oxalic acid, cthylenediamine tetraacetic acid, and citric acid, preferably citric acid, a physiologically acceptable base, preferably sodium bicarbonate, and a physiologically acceptable salt, such as calcium chloride, potassium chloride and sodium chloride, preferably sodium chloride. The molar ranges of acid:base:salt is generally about 0.1 to 0.0001M (acid): 1 to 0.001M (base): 10 to 0.01M (salt); with 0.01–0.001M (acid): 0.1 to 0.01M (base): 1 to 0.01M(salt), preferred; and 0.001M (acid): 0.01M (base): 0.1M(salt), most preferred. Typically, the concentration of lactoferrin on the surface of a composition treated in accordance with the inventive method is from about 0.0001 to about 10 mg/sq.inch.

DETAILED DESCRIPTION OF THE PREFERRED EMBODIMENTS

The LF useful in accordance with the present invention include LF isolated from mammalian sources (humans, cows, sows, mares, transgenic animals and the like), biological secretions such as colostrum, transitional milk, matured milk, milk in later lactation, and the like, or processed products thereof such as skim milk and whey. Also useful is recombinant LF cloned-expressed in either procaryotic and eucaryotic cells. The LF is isolated by any conventional method, such as by chromatography, ion-exchanger, molecular-sieve or affinity column. Suitable LF also is commercially available from DMV International Nutritionals, the Netherlands; Morinaga Milk Company, Japan; BioPole, Belgium; and Avonmore-Waterford, USA.

The LF is immobilized on a naturally occurring substrate. Such substrates include organic compounds, which attach to the LF protein to the N-terminus. Most preferably, the substrate is a galactose-rich polysaccharide. Suitable galactose-rich polysaccharides include galactose derivatives comprising galactose, anhydrogalactose, 2-Ome-galactose, and 4-Ome-galactose, among others. The galactose-rich polysaccharides can be purchased or extracted from commercial agars by known methods. Other suitable biologically active substrates include proteins, such as collagen, denatured collagen (gelatin), fibronectin, and casein; polysaccharides, such as mucin, heparan-sulfates, carrageenan, and cellulose; nucleic acids and their nucleotides, such as deoxyribonucleic acid and adenosine triphosphate; and lipids such as triglycerides.

The LF is immobilized on the substrate using any suitable technique. For example, LF can be immobilized simply by mixing the LF with the biologically active substrate in a suitable medium, such as deionized water. The immobilization process is dependent on the quality of the substrate as well as the quality of the LF. For example, in most of the commercially available lactoferrins the level of impurities (range: 4–10%), degree of non-specific cidal activity (range: 20–40%), and extent of protein denaturation (range: 10–25%) vary. Consequently, the amount of substrate and the amount of LF to be used in the immobilization reaction will depend, inter alia, on the choice of starting materials. The immobilization technique and the amounts of substrate and LF will be readily determinable by a skilled artisan without undue experimentation.

Immobilization neutralizes the cationic effect of peptide fragments and eliminates the undesirable, non-specific cidal activity of LF. Without intending to be limited by a theory of operation, it is believed that immobilization gives structural stability and bio-functional specificity to LF. Immobilized LF molecules demonstrate a molecular orientation similar to their orientation on mammalian mucosa and the immobilized LF avidly binds to tissue surfaces with a high affinity. This property facilitates the retention and carry-through of LF even when applied during an early stage of meat processing.

In preferred embodiments, the immobilized LF is combined with native LF. The molecular ratio of immobilized versus native LF is important in the specificity, broad-spectrum activity, and molecular stability of both the immobilized and the native LF. Furthermore, the interplay of immobilized LF and native LF generates a potent MBA activity. Mixtures of immobilized LF and native LF in a ratio of from about 0.25:1 to about 1:10, preferably from about 1:1 to about 1:2 of native LF to immobilized LF, most preferably 1:1 ratio have been found to provide the greatest microbial blocking activity.

Mixtures of immobilized LF and native LF are formed by adding excess LF to the substrate. In a representative embodiment, from about 0.001% wt/vol to about 2.5% wt/vol, preferably from about 0.5% wt/vol to about 2.0% wt/vol, most preferably about 1% wt/vol of LF is added to an solution containing 0.01% wt/vol galactose-rich polysaccharide. If no native LF is present (meaning that 100% of the LF is immobilized) the microbial blocking activity of the formulation will not be affected, however, retention of LF when sprayed onto the product surface will be reduced. If too much LF is added, undesirable non-specific antimicrobial properties will become significant.

In a preferred embodiment, the aqueous solution is buffered with a combination of a physiologically acceptable acid, such as oxalic acid, ethylenediamine tetraacetic acid, or citric acid, preferably citric acid, a physiologically acceptable base, preferably sodium bicarbonate, and a physiologically acceptable salt such as calcium chloride, potassium chloride or sodium chloride, preferably sodium chloride. The citrate and bicarbonate ratio in the buffer is significant for co-ordinated metal binding properties of LF, which play an important factor in enhancing the stasis effect and microbial blocking activity of the LF. The molar ranges of acid:base:salt is typically about 0.1 to 0.0001M (acid): 1 to 0.001M (base): 10 to 0.01M (salt); with 0.01–0.01M (acid): 0.1 to 0.01M (base): 1 to 0.1M(salt), preferred; and 0.001M (acid): 0.01M (base ): 0.1M(salt), most preferred.

The immobilized LF is useful with any product prone to microbial contamination or proliferation. Representative products include processed and unprocessed foodstuffs for human or for animal consumption. The immobilized LF is especially useful in treating whole muscle and ground meat products, including beef products, pork products and poultry products, such as sausages, salamis, hotdogs and the like. In addition, LF is useful in treating processed deli meats such as sliced chicken, ham, pork, turkey and the like. The present invention is also of use with medicines and drugs taken into the bodies of humans or other animals, or applied topically.

The immobilized LF is effective in treating a wide variety of microbes including bacteria, fungi, protozoa and viruses. It has been found especially useful effective in treating food-borne pathogens, food-borne radiation-resistant bacteria, and food spoilage microorganisms. Representative bacteria that can be controlled by the inventive method include: enterotoxigenic *Escherichia coli*, enteropathogenic *Escherichia coli, Shigella dysenteriae, Shigella flexneri, Salmonella typhimurium, Salmonella abony, Salmonella dublin, Salmonella hartford, Salmonella kentucky, Salmonella panama, Salmonella pullorum, Salmonella rostock, Salmonella thompson, Salmonella virschow, Campylobacter jejuni, Aeromonas hydrophila, Staphylococcus aureus, Staphylococcus hyicus, Staphylococcus epidermidis, Staphylococcus hominis, Staphylococcus warineri, Staphylococcus xylosus, Staphylococcus chromogenes, Bacillus cereus, Bacillus subtilis, Candida albicans*, and such radiation-resistant bacteria as: *Brochothrix thermospacta, Bacillus pumilus, Enterococcus faecium, Deilnococcus radiopugnans, Deinococcus radiodurans, Deinobacter grandis, Acinetobacter radioresistens, Methylobacterium radiotolerans*. It has been found especially effective in treating verotoxic *E. coli*, including the serotype O157:H7.

The immobilized LF is applied by any suitable method. Representative methods include spraying the product or washing the product during various processing steps, or coating the final product by electrostatic spray dispersion, with an aqueous suspension or solution or dehydrated powder form containing the immobilized LF. The concentration of Im-LF/native-LF mixture in aqueous formulations is typically from about 0.001% to 2.5% wt/vol, preferably about 0.5% to 2.0% wt/vol, most preferably about 1% wt/vol.

The immobilized LF is applied at any time during the preparation of the product to be treated. For example, when the product is a meat, the immobilized LF can be applied during slaughter or during the carcass wash or, if the meat product is a ground meat product, during meat grinding or homogenization. After application, the concentration of LF on the food surface typically ranges from 0.0001 to 10 mg/sq.inch of food surface, preferably 0.01 to 1 mg/sq. inch of food surface, most preferably 0.25 mg/sq. inch of food surface.

In some embodiments, an immobilized LF containing coating is applied as a fine spray to form a film on the interior surface of casings before the casings are stuffed with a batter for making sausages, salamis, hot dogs or the like. A suitable coating formulation is made by combining 1% Im-LF immobilized on GRP combined with a film-forming agent such as carrageenan, gelatin or collagen (type-I and type-II). The microbial blocking activity is retained and works to prevent microbial contamination of the encased food product.

The immobilized LF in accordance with the invention is also useful in coatings or meat packaging materials. In some embodiments, 2% immobilized LF is applied to wax-coated wrappings, cellulosic or polyethylene liners used as packing materials in meat industry. The coating is stable with full retention of its microbial blocking activity.

The following examples are intended to further illustrate the invention and are not limitations thereon. All weights are based on percent weight/volume unless otherwise clearly indicated.

EXAMPLE 1

An antimicrobial assay was performed using LF and immobilized LF (Im-LF) to demonstrate their inhibitory effects on the growth of *E. coli* serotype O157:H7 (strain ATCC43895). The *E. coli* was isolated using a microplate assay by a checker-board method from raw hamburger meat implicated in hemorrhagic colitis outbreak and known to produce shiga-like toxins I and II.e Preparation of Galactose-rich Polysaccharide A biologically active substrate containing galactose-rich polysaccharide (GRP) was prepared by mixing ten grams of solid agar (Bacteriological grade, purchased from DIFCO laboratories) with 100 ml of deionized water. After constant stirring for 1 hour, the soluble extract was passed through a sintered glass filter. The filtrate was dialyzed against distilled water, and the absorption maxima of the dialysate was determined using a UV spectrophotometer. The agar extract solution was freeze-dried and stored at room temperature.

A portion of the agar extract was hydrolyzed in 4M trifluoroacetic acid at 100° C. for 4 hours for carbohydrate analysis and the monosaccharides were quantitated as alditol acetates by gas-liquid chromatography. Chemical analysis revealed that the extract was composed mainly of galactose-derivatives. The relative molar proportions were as follows: galactose, 1; 3,6-anhydrogalactose, 0.2; 2-Ome-galactose, <0.05; 4-Ome-galactose, <0.05.

Preparation of Immobilized LF/LF Mixture

A mixture of Im-LF and native LF was prepared by mixing a solution of GRP (1% wt/vol) in deionized water with LF (1% wt/vol), obtained from cheese-whey fractionation (also in deionized water) in a 1:100 ratio. The mixture was kept at room temperature with gentle stirring for 90 minutes. The formation of Im-LF was confirmed by gel-filtration chromatography using Sephacryl S-200 HR column.

Sample Preparation

Sterile solutions of citric acid, sodium bicarbonate, and GRP were prepared and 50 μl aliquots were added, each in duplicate, to the horizontal lanes of a sterile 96-well microtiter plate. A volume of 50 μl of bacterial suspension (about $10^3$ or $10^6$ cells/ml) prepared in saline, was added to each sample. Additionally, a sample was prepared containing a mixture of GRP, citric acid, sodium bicarbonate, and sodium chloride. Appropriate amounts of sterile deionized water was added to adjust the final volume of fluid in each well to 200 µl. The final concentration of each sample is reported in Table 1 below.

Im-LF/LF mixture samples were prepared in double-strength trypticase soy broth growth media and a volume of 100 µl of the resulting solutions was added, each in duplicate wells, to the vertical columns of the microtiter plate. A volume of 50 µl of bacterial suspension, about $10^3$ or $10^6$ cells/ml, prepared in saline, was added to the duplicate wells, respectively. Additionally, a mixture containing Im-LF/LF, citric acid, sodium bicarbonate, and sodium chloride was prepared. Appropriate amount of sterile deionized water was added to each sample to adjust the final volume of fluid in each well to 200 µl. The concentrations of each sample are reported in Table 1 below.

Sample Assay

All the samples, plus a control, were incubated at 37° C. The bacterial growth was monitored at different time intervals as turbidity change in culture media by measuring OD (optical density) at 600 nm in a microplate reader. Wells containing growth media without bacteria served as sterility control, whereas the wells with growth media and bacteria without test compounds served as positive growth control. The antimicrobial activity of a test substance was estimated as % growth relative to the positive growth control. The results after incubating the samples for 24 hours are reported in Table 1.

TABLE 1

| SAMPLE | GROWTH (%) |
|---|---|
| A) Control (trypticase soy broth) | 100 |
| B) 0.001M citric acid | 103 |
| C) 0.01M sodium bicarbonate | 112 |
| D) 0.1M sodium chloride | 100 |
| E) 0.01% weight/volume GRP | 125 |
| F) Mixture of B + C + D + E | 125 |
| G) 1% LF | 36 |
| H) 1% Im-LF/LF mixture | 28 |
| I) 1% Im-LF/LF mixture in B + C + D | 0 |

Both the LF and immobilized LF/LF mixture reduced the growth of the *E. coli*. However, the Im-LF/LF mixture in buffer solution totally inhibited such growth.

EXAMPLE 2

An antimicrobial assay was performed using buffer solutions containing mixtures of 1% wt/vol LF and 1% wt/vol Im-LF or mixtures of 0.5% wt/vol LF and 0.5% wt/vol Im-LF 0.5% to demonstrate their ability to inhibit the growth-multiplication of different cell densities of *E. coli* O157:H7 strain ATCC43895.

GRP-immobilized 2% wt/vol Im-LF/native LF mixture was prepared in deionized water as described in Example 1 above. A buffer solution was prepared by combining citric acid (0.002M), sodium bicarbonate (0.02M), and sodium chloride (0.2M) in deionized water. The buffer solution was then sterilized by autoclaving.

The 1% mixture was then prepared by combining the Im-LF/native LF solution and the buffer solution, under aseptic conditions, at 1:1 ratio. The final composition of the 1% mixture is shown in TABLE 2.

TABLE 2

| | |
|---|---|
| native LF (1% wt/vol) | 10.00 g |
| immobilized LF (1% wt/vol) | 10.00 g |
| GRP (1% wt/vol) | 10.00 ml |
| Citric acid (0.001M) | 0.19 g |
| Sodium bicarbonate (0.01M) | 0.84 g |
| Sodium chloride (0.1M) | 5.8 g |
| Deionized water (adjusted to) | 1.00 liter |

A 0.5% mixture was prepared by adding additional deionized water to the 1% wt/vol mixture solution.

Samples were prepared as described in Example 1 above, except that four samples were made from each solution and the bacterial density of each solution was varied as reported in Table 3. An assay was performed according to the method described in Example 1.

The results shown in Table 3 are end-point data obtained after 24 hours of incubation at 37° C.

TABLE 3

| | % GROWTH | | |
|---|---|---|---|
| BACTERIAL DENSITY | Control | 0.5% Formulation | 1% Formulation |
| $10^4$ cells/ml | 100 | 0 | 0 |
| $10^5$ cells/ml | 100 | 0 | 0 |
| $10^6$ cells/ml | 100 | 8 | 0 |
| $10^7$ cells/ml | 100 | 27 | 11 |

It can be seen that the 0.5% mixture blocked the growth-multiplication of $10^5$ cells of *E. coli* O157:H7/ml for 24 hours and the 1% mixture demonstrated an increase of one-log antimicrobial activity and effectively blocked $10^6$ cells of *E. coli* O157:H7/ml for 24 hours.

Similar antimicrobial experiments were also performed and comparable results were obtained with an additional four *E. coli* O157:H7 strains from American Type Culture Collection: (1) ATCC43888, enterotoxigenic isolate that does not produce either shiga-like toxin I or II; (2) ATCC43889, fecal isolate from patient with hemolytic uremic syndrome and produces shiga-like toxin II; (3) ATCC43890, enterotoxigenic isolate that produces shiga-like toxin I; (4) ATCC43894, fecal isolate from outbreak of hemorrhagic colitis and produces shiga like toxins I and II.

EXAMPLE 3

An antimicrobial assay was performed using the 1% mixture prepared in accordance with Example 2 to demonstrate its ability to inhibit the growth-multiplication of different microorganisms. Samples were prepared as described in Example 1 above, except that two samples were made for each microbe to be tested and the bacterial density in the samples was $10^3$ and each $10^6$ cells/ml, respectively and that the growth media used for each bacteria varied as is reported in Table 4.

An assay was performed according to the method described in Example 2. The results are shown in Table 4 below. The microbial growth in the Control (Growth media) was considered as 100%.

TABLE 4

| MICROORGANISM | Control (Broth) | % GROWTH | |
| --- | --- | --- | --- |
| | | $10^3$ cells/ml | $10^6$ cells/ml |
| Enterotoxigenic E. coli H10407 | Tryptic-soy | 0 | 0 |
| Enteropathogenic E. coli | Tryptic-soy | 0 | 0 |
| Shigella dysenteriae | Tryptic-soy | 0 | |
| Shigella flexneri SFL1070-15 | Tryptic-soy | 0 | 0 |
| Salmonella typhimurium R10 | Tryptic-soy | 0 | 0 |
| Salmonella abony NCTC6017 | Tryptic-soy | 0 | 0 |
| Salmonella dublin NCTC9676 | Tryptic-soy | 0 | 0 |
| Salmonella hartford HNCMB10063 | Tryptic-soy | 0 | 0 |
| Salmonella kentucky NCTC5799 | Tryptic-soy | 0 | 0 |
| Salmonella panama NCTC5774 | Tryptic-soy | 0 | 0 |
| Salmonella pullorum NCTC5776 | Tryptic-soy | 0 | 0 |
| Salmonella rostock NCTC5767 | Tryptic-soy | 0 | 0 |
| Salmonella thompson NCTC5740 | Tryptic-soy | 0 | 0 |
| Salmonella virschow NCTC5742 | Tryptic-soy | 0 | 0 |
| Campylobacter jejuni ATCC33560 | Brucella Albimi | 0 | 9 |
| Yersinia enterocolitica Y162 | Tryptic-soy | 0 | 0 |
| Aeromonas hydrophila CCUG14551 | Tryptic-soy | 0 | 0 |
| Staphylococcus aureus SA-43 | Nutrient | 0 | 12 |
| Staphylococcus hyicus AC-166 | Nutrient | 0 | 14 |
| Staphylococcus epidermidis AF-9 | Nutrient | 0 | 6 |
| Staphylococcus hominis AF-93 | Nutrient | 0 | 4 |
| Staphylococcus warneri AF-101 | Nutrient | 0 | 11 |
| Staphylococcus xylosus AG-12 | Nutrient | 0 | 8 |
| Staphylococcus chromogenes AD-1 | Nutrient | 0 | 20 |
| Bacillus cereus | Nutrient | 0 | 17 |
| Bacillus subtilis | Nutrient | 0 | 24 |
| Candida albicans | Saboraud | 0 | 8 |
| Radiation-resistant bacteria | | | |
| Brochothrix thermospacta ATCC11509 | Nutrient | 0 | 28 |
| Bacillus pumilus ATCC27142 | Tryptic-soy | 0 | 18 |
| Enterococcus faecium ATCC19579 | Brain-heart | 0 | 27 |
| Deinococcus radiopugnans ATCC19172 | Nutrient | 2 | 36 |
| Deinococcus radiodurans ATCC13939 | 1% Glu-Nutrient | 3 | 43 |
| Deinobacter grandis ATCC43672 | Tryptic-soy | 2 | 34 |
| Acinetobacter radioresistens ATCC43998 | Nutrient | 9 | 51 |
| Methylobacterium radiotolerans ATCC27329 | Nutrient | 7 | 45 |

The 1.0% mixture effectively inhibited all the potential Gram-negative food-borne pathogens at both cell densities. Total inhibition was demonstrated at a cell density of $10^3$ cell/ml. Near total inhibition, ranging from total inhibition to 75% inhibition, was demonstrated at a cell density of $10^6$ cells/ml.

Radiation-resistant *Brochothrix thermospacta, Bacillus pumilus* and newly emerging meat pathogen *Enterococcus faecium* was totally inhibited at $10^3$ cells/ml using the 1.0% mixture. The remaining five radiation-resistant species tested were inhibited at over 90% at the same cell densities. Inhibition of growth-multiplication demonstrated a range of about 82% to 49% at a higher density of $10^6$ cells/ml using the 1% mixture

EXAMPLE 4

The mode of action of antimicrobial formulations in accordance with the invention was demonstrated with *E. coli* O157:H7 strain ATCC43895 on various beef tissues.
Microbial Adhesion Assay

*E. coli* O157:H7, strain ATCC43895, was grown in tryptic soy broth at 37° C. overnight. A loopfull of the resulting culture was inoculated into 5-ml tryptic soy broth containing $^3$H-thymidine (20 Ci) and incubated for 7 hours at 37° C. to incorporate $^3$H-thymidine into the bacteria's DNA. The labeled *E. coli* were harvested by centrifugation and the cell density adjusted to an OD of 0.02 (approximately $10^7$ bacterial/ml) at 600 nm using a photometer. Total plate counts were simultaneously performed and a standard curve was plotted between bacterial counts and corresponding $^3$H-thymidine labeled bacterial radioactivity.

Two ml volumes of $^3$H-labeled bacteria (about $2 \times 10^7$ cells) were incubated at room temperature in a 20 ml glass scintillation vial with approximately 0.4 g of beef tissue (four samples each of lean, fat or surface tissue from neck) to give the bacteria the opportunity to adhere to the tissue samples. After 2 hours, the non-adherent bacteria were aspirated into a second scintillation vial. Each of the three sets of samples containing the adherent bacteria were then treated with either water, saline (0.5%), lactic acid (2%), LF (1%), and the buffer solution containing 1% GRP-immobilized LF and native LF in order to detach the tissue-adherent bacteria. The treatment solutions were aspirated into another scintillation vial. Finally, the treated tissue sample was digested with 2-ml of tissue homogenizer (Scintigest, Fisher Scientific) overnight at 55° C. in a waterbath-shaker. A 10-ml volume of scintillation cocktail (ScintiSafe Gel, Fisher Scientific) was added to the homogenate and the radioactivity (DPM, disintegrations per minute) was measured in a scintillation counter (Tri-Carb 2100TR, Packard Instruments).

The results are shown in TABLE 5.

TABLE 5

| WASH TREATMENT | % BACTERIAL CELLS DETACHED IN 1-MINUTE | | |
|---|---|---|---|
| | Lean tissue | Fat tissue | Surface tissue (neck) |
| Water | 73 | 64 | 68 |
| Saline (0.5%) | 87 | 72 | 75 |
| Lactic acid (2%) | 75 | 68 | 62 |
| LF (1%) | 90 | 85 | 78 |
| Formulation (1%) | 99 | 96 | 94 |

Approximately, $10^4$ cells of *E. coli* O157:H7 were initially attached to each of the beef tissue samples. Wash with 1% LF solution demonstrated an effective bacterial detachment. The 1% formulation demonstrated a maximum bacterial detachment profile of 99% with lean tissues, 96% with fat tissues, and 94% with surface tissues from beef. Wash treatments lasting longer than 2 minutes using the 1% formulation demonstrated detachment profiles at 100%.

Similar results were obtained using four additional strains of *E. coli* O157:H7 from the American Type Culture Collection: (1) ATCC43888, (2) ATCC43889, (3) ATCC43890, and (4) ATCC43894.

EXAMPLE 5

The efficacy of microbial detachment of *E. coli* O157:H7 from beef tissue using a buffer solution containing 1% immobilized LF and native LF was tested in a 10-second wash with a digitally simulated spray system ($DS^3$).

Digitally Simulated Spray System

The $DS^3$ was specially engineered to simulate the conditions of a beef processing plant. The $DS^3$ consists of a programmable belt-line to carry meat through a total of 12 processing chambers including 6 spray-, 5 pause- and 1 meat loading-chambers. The spray chambers were connected to individual delivery tanks (2-gallon capacity) via digitally-controlled pumps with adjustable spray flow, spray time, pause, etc. These 6 spray chambers were connected into individual fluid collectors.

Sample Preparation

A meat tissue (about 4 sq. inch area) was fixed in the center of a stainless steel loading frame, located inside a beta-ray shielded acrylic box. A sterile bactainer, with an area of 1 sq. inch×0.5 inches in height and an open stainless steel hollow with a sharp-edged square end, was firmly pressed into the meat. A 5-ml volume of $^3H$-thymidine labeled *E. coli* O157:H7 cells (about 5 x $10^7$ cells) was inoculated onto the meat surface exposed inside the bactainer and the interaction was allowed for 2 hours at room temperature. The non-attached bacterial cells were aspirated into a scintillation vial. The bactainer was removed and the loading frame with $^3H$-thymidine labeled *E. coli* O157:H7 was removed from the acrylic box and mounted and locked on the meat-loading chamber of the equipment.

Sample Treatment

A set of three samples were treated with a sanitizing assembly treatment that simulated the time/temperature/spray pressure/pause typically employed during commercial beef slaughter processing. The sanitizing assembly consisted of five spray washing steps, 10-seconds each, consisting of spraying with: water, 2% lactic acid, hot water (180° F., for 30 seconds), water, and 2% lactic acid, respectively. Samples were also treated using the standard assembly with the addition of the 1% formulation in each step.

Sample Assay

After treatment, the loading frame was dismounted and placed in the beta-ray shielded acrylic box. Six random samples (about 0.5 g wt) were excised from the area previously inoculated with $^3$11-thymidine labeled *E. coli* O157:H7 cells. The samples were digested with 4-ml of tissue homogenizer (Scintigest, Fisher Scientific) overnight at 55° C. in a waterbath-shaker. A 10-ml volume of scintillation cocktail (ScintiSafe Gel, Fisher Scientific) was added to the homogenate and the radioactivity (DPM, disintegrations per minute) was measured in a scintillation counter (Tri-Carb 2100TR, Packard Instruments).

The results of the efficacy testing are shown in TABLE 6.

TABLE 6

| EXPERIMENT | % *E. COLI* O157:H7 DETACHMENT (/GM TISSUE) | |
|---|---|---|
| | Sanitizing Assembly | Sanitizing Assembly + 1% Formulation |
| Run-1 | 72.0% | 99.9% |
| Run-2 | 68.1% | 100.0% |
| Run-3 | 76.6% | 98.8% |
| Average | 72.2% | 99.6% |

The efficacy of a regular sanitizing assembly averaged 72.2% per gm of beef tissue. The sanitizing assembly coupled with the 1% formulation spray demonstrated 100% efficacy in Run-2 with an average 99.6% *E. coli* detachment per gm of beef tissue, between three experimental runs.

I claim:

1. A method for reducing the microbial contamination of a meat product, comprising treating the meat product with a sufficient amount of lactoferrin immobilized on a naturally occurring substrate via the N-terminus region of the lactoferrin to reduce microbial contamination.

2. The method in accordance with claim 1 wherein the naturally occurring substrate is a protein, a polysaccharide, cellulose, a nucleic acid, a nucleotide or a lipid.

3. The method in accordance with claim 1 wherein the naturally occurring substrate is collagen, gelatin, fibronectin, casein, mucin, heparan-sulfate, carrageenan, deoxyribonucleic acid, adenosine triphosphate or a triglyceride.

4. The method in accordance with claim 2, wherein the naturally occurring substrate is a galactose-rich polysaccharide that comprises mainly galactose residues and derivatized galactose residues.

5. The method in accordance with claim 1 further comprising applying an aqueous solution containing a mixture of the immobilized lactoferrin and native lactoferrin.

6. The method in accordance with claim 5 wherein the concentration of the mixture in the aqueous solution is from about 0.001 to about 2.5% wt/vol.

7. The method in accordance with claim 6 wherein the ratio of immobilized lactoferrin to native lactoferrin in the mixture is in a ratio of from about 1:1 to about 1:10.

8. The method in accordance with claim 6 wherein the ratio of native lactoferrin to immobilized lactoferrin in the mixture is in a ratio of from about 1:1 to about 1:2.

9. The method in accordance with claim 8 wherein the mixture comprises about 1% wt/vol immobilized lactofeltin and about 1% wt/vol native lactoferrin.

10. The method in accordance with claim 5 wherein the aqueous solution further comprises a buffer system.

11. The method in accordance with claim 10 wherein the buffer system includes a physiologically acceptable acid, a physiogyically acceptable base, and a physiologically acceptable salt.

12. The method in accordance with claim 11 wherein the physiologically acceptable acid is oxalic acid, cthylenediamine tetraacetic acid, or citric acid, the physiologically acceptable base is sodium bicarbonate, and the physiologically acceptable salt is calcium chloride, potassium chloride or sodium chloride.

13. The method in accordance with claim 2, wherein the microbe is enterotoxigenic *Escherichia coli*, enteropathogenic *Escherichia coli*, *Shigella dysenteriae*, *Shigella flexneri*, *Salmonella typhimurium*, *Salmonella abony*, *Salmonella dublin*, *Salmonella hartford*, *Salmonella kentucky*, *Salmonella panama*, *Salmonella pullorum*, *Salmonella rostock*, *Salmonella thompson*, *Salmonella virschow*, *Campylobacter jejuni*, *Aeromonas hydrophila*, *Staphylococcus aureus*, *Staphylococcus hyicus*, *Staphylococcus epidermidis*, *Staphylococcus hominis*, *Staphylococcus warneri Staphylococcus xylosus*, *Staphylococcus chromogenes*, *Bacillus cereus*, *Bacillus subtilis*, *Candida albicans*, *Brochothrix thermospacta*, *Bacillus pumilus*, *Enterococcus faecium*, *Deinococcus radiopugnans*, *Deinococcus radiodurans*, *Deinobacter grandis*, *Acinetobacter radioresistens*, or Methylobacterium radiotolerans.

14. The method in accordance with claim 13, wherein the microbe is a verotoxic *Escherichia coli*.

15. The method in accordance with claim 14, wherein the verotoxic *Escherichia coli* is the serotype O157:H7.

16. The method in accordance with claim 1 wherein the concentration of lactoferrin on the surface of the meat product is from about 0.0001 to about 10 mg/sq.inch.

17. The method in accordance with claim 16 wherein the concentration of lactoferrin on the surface of the meat product is from about 0.01 to about 1 mg/sq.inch.

18. The method in accordance with claim 1 wherein meat product is beef product, a pork product, or a poultry product.

19. A method for reducing the microbial contamination of a meat product, comprising applying to the meat product an aqueous buffer solution containing
   a physiologically acceptable acid selected from the group consisting of oxalic acid, ethylenediamine tetraacetic acid, and citric acid;
   a physiologically acceptable base; and
   a physiologically acceptable salt selected from the group consisting of calcium chloride, potassium chloride, and sodium chloride, wherein the ratio of acid to base to salt is 0.1 to 0.0001M (acid): 1 to 0.0001M (base): 10 to 0.01M (salt); and the buffer solution containing a mixture of native lactoferrin and lactoferrin immobilized via the N-terminus region of the lactoferrin on a galactose-rich polysaccharide that comprises mainly galactose residues and derivatized galactose residues, or on a collagen, gelatin, fibronectin, casein, mucin, heparan-sulfate, carrageenan, deoxyribonucleic acid, adenosine triphosphate or a triglyceride, in a native lactoferrin to immobilized lactoferrin ratio of from about 1:1 to about 1:2 and in a concentration of from about 0.001 to about 2.5 wt/vol.

20. The method in accordance with claim 21, wherein the lactoferrin is immobilized on a galactose-rich polysaccharide that comprises mainly galactose residues and derivatized galactose residues.

21. The method in accordance with claim 19 wherein the mixture comprises about 1% wt/vol immobilized lactoferrin and about 1% wt/vol native lactoferrin.

22. The method in accordance with claim 19 wherein the physiologically acceptable acid is citric acid, the physiologically acceptable base is sodium bicarbonate and the physiologically acceptable salt is sodium chloride.

23. The method in accordance with claim 22, wherein the microbe is enterotoxigenic *Escherichia coli*, enteropathogenic *Escherichia coli*, *Shigella dysenteriae*, *Shigella flexneri*, *Salmonella typhimurium*, *Salmonella abony*, *Salmonella dublin*, *Salmonella hartford*, *Salmonella kentucky*, *Salmonella panama*, *Salimonella pullorum*, *Salmonella rostock*, *Salmonella thompson*, *Salmonella virschow*, *Campylobacter jejuni*, *Aeromonas hydrophila*, *Staphylococcus aureus*, *Staphylococcus hyicus*, *Staphylococcus epidermidis*, *Staphylococcus hominis*, *Staphylococcus warneri*, *Staphylococcus xylosus*, *Staphylococcus chromogenes*, *Bacillus cereus*, *Bacillus subtilis*, *Candida albicans*, *Brochothrix thermospacta*, *Bacillus pumilus*, *Enterococcus faecium*, *Deinococcus radiopugnans*, *Deinococcus radiodurans*, *Deinobacter grandis*, *Acinetobacter radioresistens*, or *Methylobacterium radiotolerans*.

24. The method in accordance with claim 23, wherein the microbe is a verotoxic *Escherichia coli*.

25. The method in accordance with claim 24, wherein the verotoxic *Escherichia coli* is the serotype O157:H7.

26. The method in accordance with claim 22 wherein the concentration of lactofenrin on the surface of the meat product is from about 0.0001 to about 10 mg/sq.inch.

27. The method in accordance with claim 26 wherein the concentration of lactofenrin on the surface of the meat product is from about 0.01 to about 1 mg/sq.inch.

28. The method in accordance with claim 23 wherein the meat product is a beef product, a pork product, or a poultry product.

29. A composition of matter comprising an aqueous solution containing isolated lactoferrin immobilized on a naturally occurring substrate via the N-terminus region of the lactoferrin.

30. The composition in accordance with claim 29 wherein the naturally occurring substrate is a protein, a polysaccharide, cellulose, a nucleic acid, a nucleotide, or a lipid.

31. The composition in accordance with claim 30 wherein the naturally occurring substrate is collagen, gelatin, fibronectin, casein, mucin, heparan-sulfate, carrageenan, deoxyribonucleic acid, adenosine triphosphate or a triglyceride.

32. The composition in accordance with claim 29, wherein the naturally occurring substrate is a galactose-rich polysaccharide that comprises mainly galactose residues and derivatized galactose residues.

33. The composition in accordance with claim 29, further comprising native lactoferrin.

34. The composition in accordance with claim 33 wherein the concentration of immobilized lactoferrin and native lactofenrin in the aqueous solution is from about 0.05% wt/vol to about 2.5% wt/vol.

35. The composition in accordance with claim 34 wherein the ratio of immobilized lactoferrin to native lactoferrin is in a ratio of from about 1:1 to about 1:10.

36. The composition in accordance with claim 34 wherein the ratio of native lactoferrin to immobilized lactoferrin is in a ratio of from about 1:1 to about 1:2.

37. The composition in accordance with claim 33, wherein the aqueous solution comprises about 1% wt/vol immobilized lactoferrin and about 1% wt/vol native lactoferrin.

38. The composition in accordance with claim 33 wherein the aqueous solution further comprises a buffer system.

39. The composition in accordance with claim 38 wherein the buffer system contains a physiologically acceptable acid, a physiologically acceptable base, and a physiologically acceptable salt.

40. The composition in accordance with claim 39 wherein the physiologically acceptable acid is oxalic acid, ethylenediamine tetraacetic acid, or citric acid, the physiologically acceptable base is sodium bicarbonate, and the physiologically acceptable salt is calcium chloride, potassium chloride or sodium chloride.

41. A composition of matter comprising an aqueous buffer solution containing:
  a physiologically acceptable acid selected from the group consisting of oxalic acid, ethylenediamine tetraacetic acid, and citric acid;
  a physiologically acceptable base; and
  a physiologically acceptable salt selected from the group consisting of calcium chloride, potassium chloride, and sodium chloride, wherein the ratio of acid to base to salt is 0.1 to 0.0001M (acid): 1 to 0.01M (base); 10 to 0.01M (salt); and the buffer solution containing a mixture of native lactoferrin and lactoferrin immobilized via the N-terminus region of the lactoferrin on a galactose-rich polysaccharide that comprises mainly galactose residues and derivatized galactose residues, or on a collagen, gelatin, fibronectin, casein, mucin, heparan-sulfate, carrageenan, deoxyribonucleic acid, adenosine triphosphate or a triglyceride, in a native lactoferrin to immobilized lactoferrin ratio of from about 1:1 to about 1:2 and in a concentration of from about 0.001 to about 2.5 wt/vol.

42. The method in accordance with claim 41, wherein the lactoferrin is immobilized on a galactose-rich polysaccharide that comprises mainly galactose residues and derivatized galactose residues.

43. The composition in accordance with claim 41, wherein the mixture comprises about 1% wt/vol immobilized lactoferrin and about 1% wt/vol native lactoferrin.

44. The composition in accordance with claim 41, wherein the physiologically acceptable acid is citric acid, the physiologically acceptable base is sodium bicarbonate and the physiologically acceptable salt is sodium chloride.

45. A method for reducing the microbial contamination of a composition subject to microbial contamination comprising treating the composition with a sufficient amount of isolates lactoferrin immobilized on a naturally occurring substrate via the N-terminus region of the lactoferrin to reduce microbial contamination.

46. The method in accordance with claim 45 wherein the naturally occurring substrate is a protein, a polysaccharide, cellulose, a nucleic acid, a nucleotide or a lipid.

47. The method in accordance with claim 46 wherein the naturally occurring substrate is collagen, gelatin, fibronectin, casein, mucin, heparan-sulfate, carrageenan, deoxyribonucleic acid, adenosine triphosphate or a triglyceride.

48. The method in accordance with claim 45, wherein the naturally occurring substrate is a galactose-rich polysaccharide that comprises mainly galactose residues and derivatized galactose residues.

49. The method in accordance with claim 45 further comprising applying an aqueous solution containing a mixture of immobilized lactoferrin and native lactoferrin.

50. The method in accordance with claim 49 wherein the concentration of the mixture in the aqueous solution is from about 0.001 to about 2.5% wt/vol.

51. The method in accordance with claim 49 wherein the ratio of immobilized lactoferrin to native lactoferrin in the mixture is in a ratio of from about 1:1 to about 1:10.

52. The method in accordance with claim 49 wherein the ratio of native lactoferrin to immobilized lactoferrin in the mixture is in a ratio of from about 1:1 to about 1:2.

53. The method in accordance with claim 49 wherein the mixture comprises about 1% wt/vol immobilized lactoferrin and about 1% wt/vol native lactoferrin.

54. The method in accordance with claim 49 wherein the aqueous solution further comprises a buffer system.

55. The method in accordance with claim 54 wherein the buffer system contains a physiologically acceptable acid, a physiologically acceptable base, and a physiologically acceptable salt.

56. The method in accordance with claim 55 wherein the physiologically acceptable acid is oxalic acid, ethylenediamine tetraacetic acid, or citric acid, the physiologically acceptable base is sodium bicarbonate, and the physiologically acceptable salt is calcium chloride, potassium chloride or sodium chloride.

57. The method in accordance with claim 45, wherein the microbe is enterotoxigenic *Escherichia coli*, enteropathogenic *Escherichia coli, Shigella dysenteriae, Shigella flexneri, Salmonella typhimurium, Salmonella abony, Salmonella dublin, Salmonella hartford, Salmonella kentucky, Salmonella panama, Salmonella pullorulil, Salmonella rostock, Salmonella thompson, Salmonella virschow, Campylobacter jejuni, Aeromonas hydrophila, Staphylococcus aureus, Staphylococcus hyicus, Staphylococcus epidermidis, Staphylococcus hominis, Staphylococcus warneri, Staphylococcus xylosus, Staphylococcus chromogenes, Bacillus cereus, Bacillus subtilis, Candida albicans, Brochothrix thermospacta, Bacillus pumilus, Enterococcus faecium, Deinococcus radiopugnans, Deinococcus radiodurans, Deinobacter grandis, Acinetobacter radioresistens*, or Methylobacterium radiotolerans.

58. The method in accordance with claim 57, wherein the microbe is a verotoxic *Escherichia coli*.

59. The method in accordance with claim 58, wherein the verotoxic *Escherichia coli* is the serotype O157:H7.

60. The method in accordance with claim 57, wherein the concentration of lactoferrin on the surface of the composition subject to microbial contamination is from about 0.0001 to about 10 mg/sq.inch.

61. The method in accordance with claim 60, wherein the concentration lactoferrin on the surface of the composition subject to microbial contamination is from about 0.01 to about 1 mg/sq. inch.

62. A method for reducing the microbial contamination of a composition subject to microbial contamination, comprising treating the composition with an aqueous buffer solution containing:
  a physiologically acceptable acid selected from the group consisting of oxalic acid, ethylenediamine tetraacetic acid, and citric acid;
  a physiologically acceptable base; and
  a physiologically acceptable salt selected from the group consisting of calcium chloride, potassium chloride, and sodium chloride, wherein the ratio of acid to base to salt is 0.1 to 0.0001M (acid): 1 to 0.001M (base): 10 to 0.01M (salt); and the buffer solution containing a mixture of native lactoferrin and lactoferrin immobilized via the N-terminus region of the lactoferrin on a galactose-rich polysaccharide that comprises mainly galactose residues and derivatized galactose residues, or on a collagen, gelatin, fibronectin, casein, mucin, heparan-sulfate, carrageenan, deoxyribonucleic acid, adenosine triphosphate or a triglyceride, in a native lactoferrin to immobilized lactoferrin ratio of from about 1:1 to about 1:20 and in a concentration of from about 0.001 to about 2.5 wt/vol.

63. The method in accordance with claim 62, wherein the lactoferrin is immobilized on a galactose-rich polysaccharide that comprises mainly galactose residues and derivatized galactose residues.

64. The method in accordance with claim 63 wherein the mixture comprises about 1% wt/vol immobilized lactoferrin and about 1% wt/vol native lactoferrin.

65. The method in accordance with claim 62 wherein the physiologically acceptable acid is citric acid, the physiologically acceptable base is sodium bicarbonate and the physiologically acceptable salt is sodium chloride.

66. The method in accordance with claim 62, wherein the microbe is enterotoxigenic *Escherichia coli*, enteropathogenic *Escherichia coli*, *Shigella dysenteriae*, *Shigella flexneri*, *Salmonella typhimurium*, *Salmonella abony*, *Salmonella dublin*, *Salmonella hartford*, *Salmonella kentucky*, *Salmonella panama*, *Salmonella pullorum*, *Salmonella rostock*, *Salmonella thompson*, *Salmonella virschow*, *Campylobacter jejuni*, *Aeromonas hydrophila*, *Staphylococcus aureus*, *Staphylococcus hyicus*, *Staphylococcus epidermidis*, *Staphylococcus hominis*, *Staphylococcus warneri*, *Staphylococcus xylosus*, *Staphylococcus chromogenes*, *Bacillus cereus*, *Bacillus subtilis*, *Candida albicans*, *Brochothrix thermospacta*, *Bacillus pumilus*, *Enterococcus faecium*, *Deinococcus radiopugnans*, *Deinococcus radiodurans*, *Deinobacter grandis*, *Acinetobacter radioresistens*, or *Methylobacterium radiotolerans*.

67. The method in accordance with claim 66, wherein the microbe is a verotoxic *Escherichia coli*.

68. The method in accordance with claim 67, wherein the verotoxic *Escherichia coli* is the serotype O157:H7.

69. The method in accordance with claim 11, wherein the ratio of acid to base to salt is 0.1 to 0.0001M (acid): 1 to 0.001M (base): 10 to 0.01M (salt).

70. The method in accordance with claim 69 wherein the ratio of acid to base to salt is 0.01–0.001M (acid): 0.1 to 0.01M (base): 1 to 0.1M(salt).

71. The composition in accordance with claim 39 wherein the ratio of acid to base to salt is 0.1 to 0.0001M (acid): 1 to 0.001M (base): 10 to 0.01M (salt).

72. The composition in accordance with claim 71 wherein the ratio of acid to base to salt is 0.01–0.001M (acid): 0.1 to 0.01M (base): 1 to 0.1M(salt).

73. The method in accordance with claim 55 wherein the ratio of acid to base to salt is 0.1 to 0.0001M (acid): 1 to 0.001M (base): 10 to 0.01M (salt).

74. The method in accordance with claim 73 wherein the ratio of acid to base to salt is 0.01–0.001M (acid): 0.1 to 0.01M (base): 1 to 0.1M(salt).

75. The method in accordance with claim 1, wherein the naturally occurring substrate is a galactose-rich polysaccharide comprising mainly galactose residues and derivatized galactose residues in the relative molar proportions of galactose, 1; 3,6-anhydro galactose, 0.2; 2-Ome-galactose, <0.05; 4-Ome-Galactose, <0.05.

76. The method in accordance with claim 19, wherein the galactose residues and derivatized galactose residues of the galactose-rich polysaccharide are in the relative molar proportions of galactose, 1; 3,6-anhydrogalactose, 0.2; 2-Ome-galactose, <0.05; 4-Ome-Galactose, <0.05.

77. The composition in accordance with claim 29, wherein the naturally occurring substrate is a galactose-rich polysaccharide comprising mainly galactose residues and derivatized galactose residues in the relative molar proportions of galactose, 1; 3,6-anhydrogalactose, 0.2; 2-Ome-galactose, <0.05; 4-Ome-Galactose, <0.05.

78. The composition in accordance with claim 41, wherein the galactose residues and derivatized galactose residues of the galactose-rich polysaccharide are in the relative molar proportions of galactose, 1; 3,6-anhydrogalactose, 0.2; 2-Ome-galactose, <0.05; 4-Ome-Galactose, <0.05.

79. The method in accordance with claim 45, wherein the naturally occurring substrate is a galactose-rich polysaccharide comprising mainly galactose residues and derivatized galactose residues in the relative molar proportions of galactose, 1; 3,6-anhydrogalactose, 0.2; 2-Ome-galactose, <0.05; 4-Ome-Galactose, <0.05.

80. The method in accordance with claim 62, wherein the galactose residues and derivatized galactose residues of the galactose-rich polysaccharide are in the relative molar proportions of galactose, 1; 3,6-anhydrogalactose, 0.2; 2-Ome-galactose, <0.05; 4-Ome-Galactose, <0.05.

* * * * *